US012434079B2

(12) United States Patent
Werjefelt et al.

(10) Patent No.: US 12,434,079 B2
(45) Date of Patent: Oct. 7, 2025

(54) PATHOGEN PROTECTION DEVICE

(71) Applicants: Alexander Werjefelt, Kamuela, HI (US); Christian Werjefelt, Kaneohe, HI (US); Bertil Wejefelt, Kaneohe, HI (US)

(72) Inventors: Alexander Werjefelt, Kamuela, HI (US); Christian Werjefelt, Kaneohe, HI (US); Bertil Wejefelt, Kaneohe, HI (US)

( * ) Notice: Subject to any disclaimer, the term of this patent is extended or adjusted under 35 U.S.C. 154(b) by 384 days.

(21) Appl. No.: 17/212,278

(22) Filed: Mar. 25, 2021

(65) Prior Publication Data

US 2021/0299484 A1 Sep. 30, 2021

Related U.S. Application Data

(60) Provisional application No. 63/003,006, filed on Mar. 31, 2020, provisional application No. 63/001,188, (Continued)

(51) Int. Cl.

*A62B 7/10* (2006.01)
*A42B 3/28* (2006.01)

(Continued)

(52) U.S. Cl.

CPC ................ *A62B 7/10* (2013.01); *A42B 3/288* (2013.01); *A62B 7/12* (2013.01); *A62B 9/00* (2013.01); *A62B 13/00* (2013.01); *A62B 17/04* (2013.01); *A62B 18/006* (2013.01); *A62B 18/04* (2013.01); *A62B 18/08* (2013.01); *A62B 31/00* (2013.01);

(Continued)

(58) Field of Classification Search

CPC ..... A62B 17/006; A62B 18/04; A62B 18/006; A62B 18/00; A62B 23/00; A62B 7/00; A62B 7/10; A62B 17/00; A62B 17/04; A62B 18/003; A62B 23/02; A62B 7/12; A62B 9/00; A62B 13/00; A62B 18/08; A62B 31/00; A62B 9/02; A62B 18/10;

(Continued)

(56) References Cited

U.S. PATENT DOCUMENTS

| | | | | |
|---|---|---|---|---|
| 1,004,507 A * | 9/1911 | Walz | A42B 1/046 2/4 |
| 2,413,386 A * | 12/1946 | Schulz | A41D 13/0025 2/458 |

(Continued)

FOREIGN PATENT DOCUMENTS

| | | |
|---|---|---|
| CN | 202170670 U * | 3/2012 |
| CN | 110409911 A * | 11/2019 |
| KR | 101932881 B1 * | 12/2018 |

OTHER PUBLICATIONS

English translation for CN 202170670, machine translated by Espacenet.com, translated on Jan. 2, 2024.*

(Continued)

*Primary Examiner* — Tu A Vo
(74) *Attorney, Agent, or Firm* — FRESH IP PLC

(57) ABSTRACT

A pathogen protection device includes an enclosure made of air-tight material, the enclosure is configured to seal a user's head from outside of the enclosure and allow the user to see through; and a filter is disposed on a wall of the enclosure to allow filtered air to enter and exit the enclosure, the filter is configured to remove pathogens from the filtered air.

17 Claims, 12 Drawing Sheets

Related U.S. Application Data filed on Mar. 27, 2020, provisional application No. 62/994,925, filed on Mar. 26, 2020.

(51) Int. Cl.

| | |
|---|---|
| ***A62B 7/12*** | (2006.01) |
| ***A62B 9/00*** | (2006.01) |
| ***A62B 13/00*** | (2006.01) |
| ***A62B 17/04*** | (2006.01) |
| ***A62B 18/00*** | (2006.01) |
| ***A62B 18/04*** | (2006.01) |
| ***A62B 18/08*** | (2006.01) |
| ***A62B 31/00*** | (2006.01) |
| *A61M 16/06* | (2006.01) |
| *A62B 9/02* | (2006.01) |
| *A62B 18/10* | (2006.01) |

(52) U.S. Cl.
CPC . *A61M 16/0627* (2014.02); *A61M 2202/0208* (2013.01); *A62B 9/02* (2013.01); *A62B 18/10* (2013.01)

(58) Field of Classification Search
CPC ............... A41D 13/0025; A42B 3/288; A61M 2202/0208; A61M 16/0627
See application file for complete search history.

(56) References Cited

U.S. PATENT DOCUMENTS

| | | | | | |
|---|---|---|---|---|---|
| 2,675,150 | A * | 4/1954 | Ackerman | A62B 9/04 | 224/641 |
| 3,174,300 | A * | 3/1965 | Webb | B64D 10/00 | 62/317 |
| 3,413,972 | A * | 12/1968 | Depping | A62B 18/045 | 128/201.23 |
| 3,442,427 | A * | 5/1969 | Arnell | A45F 3/08 | 224/261 |
| 3,736,927 | A * | 6/1973 | Misaqi | A62B 18/006 | 128/201.25 |
| 3,774,522 | A | 11/1973 | Marsh | | |
| 3,963,021 | A * | 6/1976 | Bancroft | A62B 18/045 | 128/201.25 |
| 4,019,508 | A * | 4/1977 | Der Estephanian | A61M 16/1065 | 128/202.19 |
| 4,091,470 | A | 5/1978 | Ryunoshin | | |
| 4,236,514 | A | 12/1980 | Moretti et al. | | |
| 4,430,995 | A * | 2/1984 | Hilton | A61M 16/0069 | 128/205.12 |
| 4,590,951 | A * | 5/1986 | O'Connor | A62B 18/006 | 128/205.12 |
| 4,620,538 | A | 11/1986 | Koegel et al. | | |
| 4,627,431 | A | 12/1986 | Werjefelt | | |
| 4,683,880 | A | 8/1987 | Werjefelt | | |
| 4,688,566 | A * | 8/1987 | Boyce | A41D 13/1123 | 128/206.19 |
| 4,864,654 | A * | 9/1989 | Schriver | A62B 17/006 | 2/84 |
| 4,998,529 | A | 3/1991 | Werjefelt | | |
| 5,116,273 | A | 5/1992 | Chan | | |
| 5,217,408 | A * | 6/1993 | Kaine | A62B 17/005 | 62/259.3 |
| 5,226,409 | A | 7/1993 | Bower | | |
| 5,301,705 | A * | 4/1994 | Zheng | E04H 15/14 | 135/125 |
| 5,331,991 | A * | 7/1994 | Nilsson | E04H 9/10 | 135/93 |
| 5,367,706 | A * | 11/1994 | Davidson | A42B 1/201 | 2/202 |
| 5,394,870 | A * | 3/1995 | Johansson | A62B 18/006 | 128/201.25 |
| 5,411,017 | A * | 5/1995 | Wong | A62B 17/04 | 128/201.25 |
| 5,548,846 | A * | 8/1996 | Bianchetti | A42B 1/0184 | 2/209.12 |
| 5,592,936 | A | 1/1997 | Thomas, Jr. et al. | | |
| 5,628,071 | A | 5/1997 | Nezer | | |
| 5,655,374 | A * | 8/1997 | Santilli | A41D 13/1218 | 2/905 |
| 5,819,728 | A | 10/1998 | Ritchie | | |
| 5,896,590 | A | 4/1999 | Fleisch | | |
| 6,233,748 | B1 | 5/2001 | Gieger | | |
| 7,007,690 | B1 * | 3/2006 | Grove | A62B 18/02 | 128/206.17 |
| 7,481,234 | B1 * | 1/2009 | Gustafson | E04H 15/425 | 135/156 |
| 9,022,034 | B2 | 5/2015 | Slaker et al. | | |
| 9,248,248 | B2 | 2/2016 | Virr | | |
| 9,617,753 | B2 * | 4/2017 | Day | E04H 15/20 | |
| 9,675,127 | B2 | 6/2017 | Guadagnin et al. | | |
| 10,448,685 | B2 | 10/2019 | Czajka et al. | | |
| 10,449,397 | B2 | 10/2019 | VanDerWoude et al. | | |
| 11,027,156 | B2 * | 6/2021 | Chessari | A62B 17/04 | |
| 2003/0192103 | A1 * | 10/2003 | Avery | A62B 17/006 | 2/69 |
| 2003/0192537 | A1 * | 10/2003 | Odell | A62B 31/00 | 128/201.25 |
| 2003/0192541 | A1 * | 10/2003 | Avery | A62B 25/00 | 128/201.22 |
| 2005/0010996 | A1 * | 1/2005 | Steinert | A62B 17/006 | 2/458 |
| 2005/0011517 | A1 * | 1/2005 | Steinert | A62B 17/006 | 128/202.19 |
| 2005/0015866 | A1 | 1/2005 | Steinert | | |
| 2006/0213523 | A1 * | 9/2006 | VanDerWoude | A41D 13/0025 | 128/863 |
| 2007/0034244 | A1 * | 2/2007 | Kwon | E04H 15/32 | 135/120.1 |
| 2007/0068520 | A1 * | 3/2007 | Laib | A62B 7/14 | 128/201.19 |
| 2007/0235031 | A1 | 10/2007 | Betz | | |
| 2007/0240719 | A1 * | 10/2007 | Duarte | A62B 18/006 | 128/205.27 |
| 2008/0110469 | A1 * | 5/2008 | Weinberg | A41D 13/1176 | 128/206.25 |
| 2008/0245364 | A1 * | 10/2008 | Patterson | A62B 7/10 | 128/201.28 |
| 2009/0004047 | A1 | 1/2009 | Hunter | | |
| 2009/0260137 | A1 * | 10/2009 | Koch | A62B 17/005 | 165/46 |
| 2009/0277451 | A1 * | 11/2009 | Weinberg | A41D 13/1176 | 128/206.16 |
| 2010/0037891 | A1 * | 2/2010 | Walker | A62B 7/12 | 128/201.23 |
| 2010/0108067 | A1 * | 5/2010 | Walker | A62B 18/006 | 128/205.24 |
| 2010/0224194 | A1 * | 9/2010 | Walker | A62B 18/02 | 128/205.24 |
| 2010/0263671 | A1 * | 10/2010 | Walker | A62B 17/04 | 128/205.25 |
| 2010/0294270 | A1 * | 11/2010 | Curran | A62B 18/045 | 128/201.23 |
| 2011/0265790 | A1 * | 11/2011 | Walker | A42B 3/286 | 128/201.23 |
| 2012/0051904 | A1 * | 3/2012 | Hagen | B62K 11/02 | 415/224 |
| 2012/0246809 | A1 * | 10/2012 | Elam | A42B 3/227 | 2/424 |
| 2013/0092164 | A1 * | 4/2013 | Curran | A62B 23/02 | 128/204.21 |
| 2013/0097769 | A1 * | 4/2013 | Tuffery | A62B 17/006 | 2/456 |
| 2013/0186279 | A1 * | 7/2013 | Dwyer | A62B 18/088 | 96/418 |
| 2013/0319408 | A1 * | 12/2013 | Zwolinsky | A62B 18/02 | 128/204.21 |

(56) References Cited

U.S. PATENT DOCUMENTS

| | | | | |
|---|---|---|---|---|
| 2015/0114389 | A1* | 4/2015 | Sernfalt | A62B 9/003 128/202.22 |
| 2015/0211534 | A1* | 7/2015 | Volmer | A62B 18/006 417/45 |
| 2015/0306432 | A1* | 10/2015 | Orofino | A62B 18/025 29/505 |
| 2015/0375019 | A1* | 12/2015 | VanDerWoude | A62B 18/003 128/201.29 |
| 2016/0090989 | A1* | 3/2016 | Volmer | F04D 29/62 415/118 |
| 2017/0189727 | A1* | 7/2017 | Hunter | A62B 18/006 |
| 2017/0361133 | A1 | 12/2017 | Yu et al. | |
| 2018/0028846 | A1* | 2/2018 | Hur | A62B 17/04 |
| 2018/0337373 | A1* | 11/2018 | Wu | A62B 9/04 |
| 2019/0143154 | A1* | 5/2019 | Gangadhar | A62B 23/02 128/202.22 |
| 2019/0289946 | A1* | 9/2019 | Perusse | A62B 18/003 |
| 2020/0060359 | A1* | 2/2020 | Jascomb | A41D 13/0025 |
| 2020/0060375 | A1* | 2/2020 | Jascomb | A41D 13/1218 |
| 2020/0232245 | A1* | 7/2020 | Ellison | F24F 3/001 |

OTHER PUBLICATIONS

English translation of CN 110409911, machine translated by Espacenet.com.*

English translation for KR 101932881, machine translated by espacenet.com, translated on Dec. 9, 2024.*

Notification of Transmittal of the International Search Report and the Written Opinion of the International Searching Authority, or the Declaration dated Aug. 5, 2021.

* cited by examiner

FIG. 1
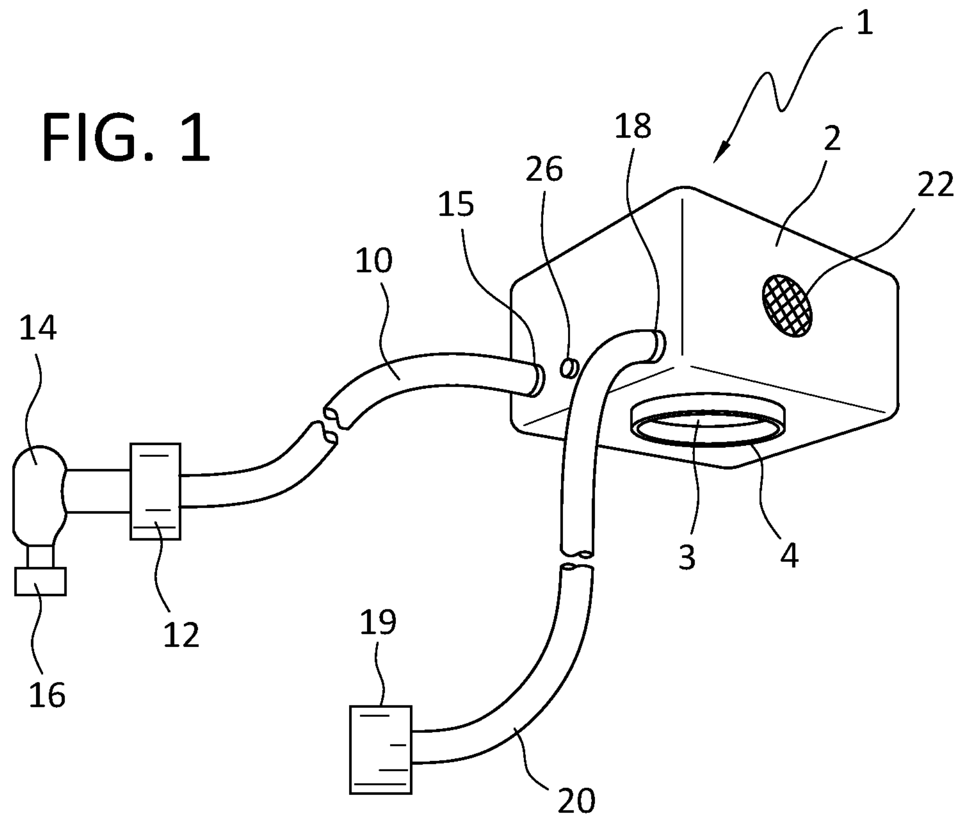
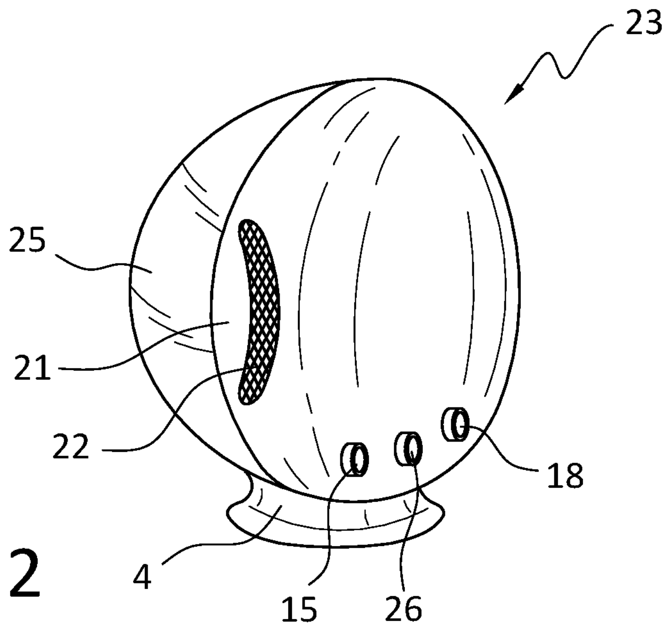
FIG. 2

FIG. 5A
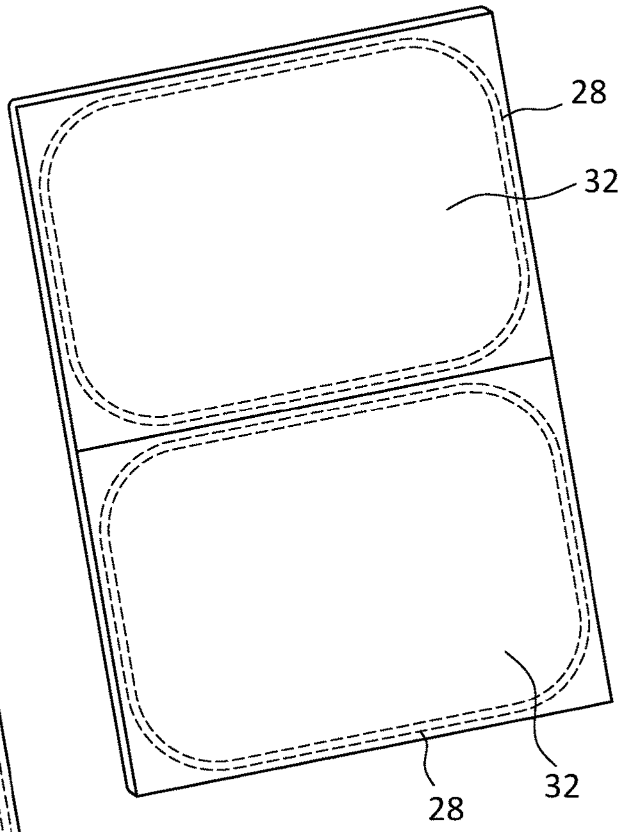
FIG. 5B
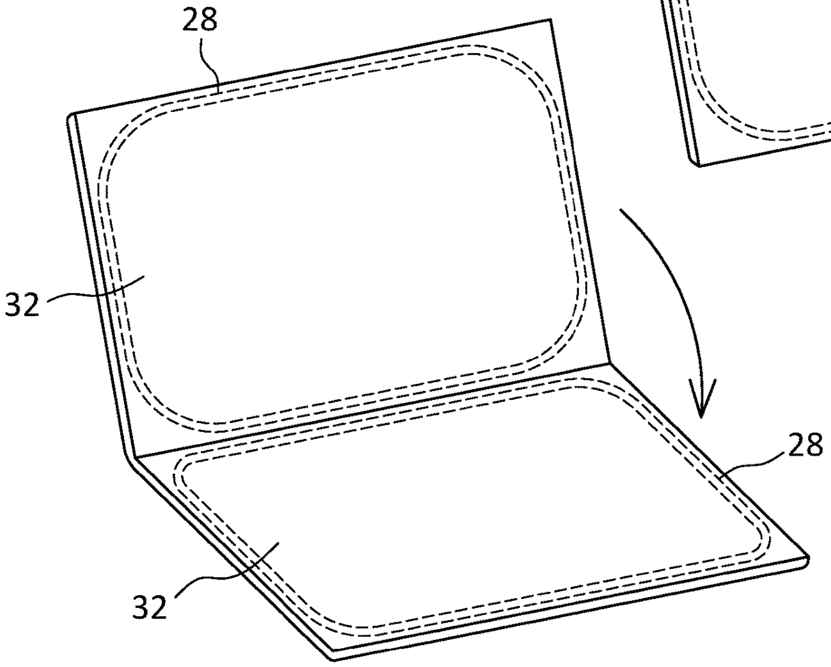
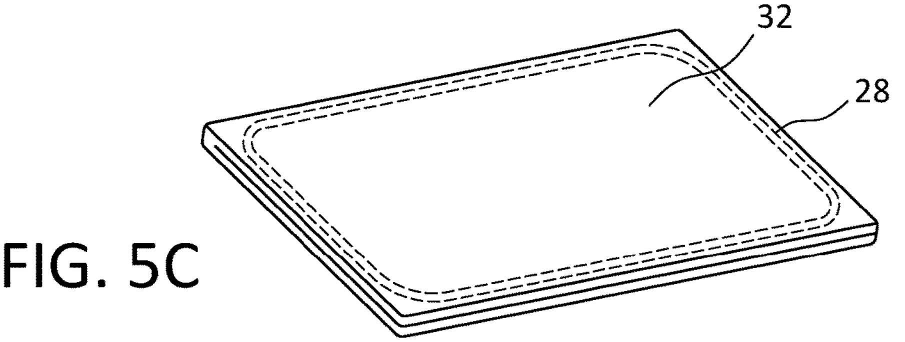
FIG. 5C

PATHOGEN PROTECTION DEVICE

RELATED APPLICATIONS

This is a nonprovisional application claiming the priorities of Provisional Applications Serial Nos. 62/994,925, 63/001,188 and 63/003,006 filed Mar. 26, 2020, 03/27/2020 and 03/31/2020, respectively, all of which are hereby incorporated by reference.

BACKGROUND OF INVENTION

Existing "hooded ventilators" and breathing hoods for air filtration can create issues where it is hard to communicate due to being composed mostly of impervious plastic. They can be bulky, uncomfortable and cumbersome to use, and difficult to produce and store in large quantities. Light weight filter hoods that retain their shape with little material, allow for sound to travel through the hood more easily, can collapse into a small form factor for storage, and be made at little cost, are valuable attributes to solve flaws prevalent in existing devices, particularly during a pandemic, where such devices may need to be produced in large quantities.

SUMMARY OF THE INVENTION

The present invention provides a pathogen protection device comprising an enclosure made of air-tight material configured to seal a user's head from the outside and allow the user to see through; and a filter is disposed on a wall of the enclosure to allow filtered air to enter and exit the enclosure.

The present invention also provides a pathogen protection device, comprising an enclosure made of air-tight material configured to enclose a user's head and allow the user to see through, the enclosure including a bottom opening for placing into or removing from the enclosure a user's head; the enclosure including side walls; at least two of the walls including a spring wire loop operably attached to the respective walls to stretch the walls outwardly.

BRIEF DESCRIPTION OF THE DRAWINGS

FIG. 1 is schematic view of a pathogen protection device embodying the present invention.

FIG. 2 is a schematic view of a helmet version of the device of FIG. 1.

FIGS. 5A-5E show a process of folding the device of FIG. 1 into a flat and compact configuration.

DETAILED DESCRIPTION OF THE INVENTION

Figure 3:
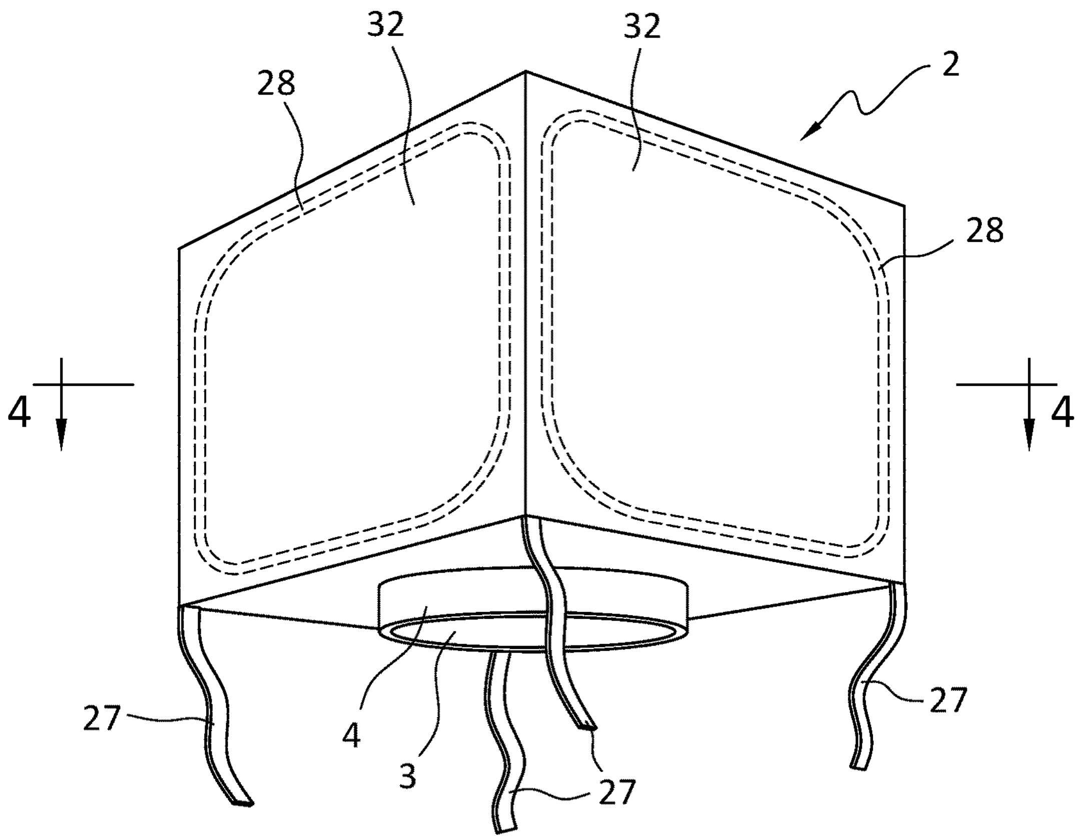
FIG. 3 is a schematic view of the enclosure showing the use of spring wire loops as a frame.

Referring to FIG. 1, a pathogen protection device 1 is disclosed. The device 1 includes an expandable enclosure 2, preferably made of foldable and flexible clear plastic sheet material, a combination of clear plastic sheet and opaque plastic sheet or air-tight fabric material, or hard rigid plastic formed into a helmet (see FIG. 2) and is worn around a person's head and sealed around the neck. When worn, the enclosure 2 completely encloses the person's head, isolating the person's head from the outside. The bottom portion of the enclosure 2 includes an opening 3 with a rubber, silicone or stretchable ring 4 to seal the enclosure around the neck. The rubber ring 4 may be replaced with a VELCRO strap to tie the bottom opening around the neck. The rubber ring 4 may be detachable from the enclosure to allow use of different sizes for different neck sizes. The ring 4 may extend over the user's shoulders as generally shown in FIG. 11C.

For the neck collar or ring 4 for either the expandable enclosure 2 or the helmet version, the ring 4 may be a rubbery, silicone or stretchy material that goes around the patient's/or caregiver's neck to seal the bottom of the enclosure to keep air from within from flowing out in the case of a patient-user. The enclosure 2 may be pressurized if needed in the case of a caregiver-user. The enclosure 2 can be made for various sizes, or there could be a mount that allows the user to attach the appropriately sized collar or ring.

The enclosure 2 may include a frame or rigid support to hold its form in expanded state during use. The enclosure 2 is preferably collapsible when not in use for ease of storage and shipment. The frame may be made of spring wire loops made of steel that can be twisted and folded flat onto itself to make the enclosure 2 to fold flat. By making the frame from spring steel wire loops, the enclosure 2 can be folded flat very easily for storage or shipping. The frame will support the material of the enclosure to create the general shape of the head gear. By using spring steel wire, a variety of shapes may be used, including square, cylindrical etc.

The enclosure 2 may also be made without the frame. In this case, air pressure is used to maintain the shape of the enclosure.

Ambient air may be pumped into the enclosure 2 through a tube 10, a filter 12, and a blower 14 powered by a battery pack or power module 16. The tube 10 is connected to an inlet port 15. Ambient air is filtered through the filter 12 to remove any pathogens that may be in the air. An accessory port 26 on the enclosure 2 may be provided for connection to a source of oxygen or other medical gas mixtures that may be needed by the user. The filter 12 will filter the incoming air prior to entering the enclosure 2 to keep the patient or caregiver safe from external pathogens. The port 26 is closed and sealed when not in use.

A housing for the blower 14 and the filter 12 may be provided with a strap that can be worn as a belt or otherwise attached to a uniform or elsewhere on the user's clothing so that the user wearing the enclosure 2 can be mobile, or the system can be easily set up for pandemic type situations. The battery pack 16 may be charged from a regular wall outlet while the unit is being used or unplugged to allow the user greater mobility.

The blower 14 may either be in front of or behind (sucking or blowing air through filter) the filter 12 that pushes air into the enclosure 2.

A filter patch 22 or an exhaust port 18 with a filter is provided on the enclosure 2 for exhalation. The filter 22 is designed to trap pathogens inside the enclosure 2 as the user exhales. The outgoing air is thus relatively free of pathogen. An exhaust tube 20 attached to the exhaust port 18 with a filter may be used instead of the filter 22. The exhaust port 18 is closed and sealed when not in use.

The filter 22 may be disposed on one or more sides of the enclosure, including the top side. The filter 22 in sheet form (patch) may be attached to the wall by sewing, adhesives, VELCRO fasteners and tape to seal the edges, or other standard means. Although the filter is shown as in patch or sheet form, the filter 22 may also be of a cartridge type that can be easily screwed on, snapped in place or otherwise attached by standard means to the enclosure. The cartridge type filter advantageously allows for quick filter replacement as needed without the need to replace the enclosure 2 when used by the same user. The filter passively filters and expels the air out from the interior of the enclosure. The filter 22 advantageously assists in better communication with the user as sound travels better through the filter than plastic. The entire enclosure 2, except in areas where clear plastic panels are used to allow the user to see out, may be made of filter sheet material.

The enclosure 2 may also have an adjustable relief valve connected to the exhaust port 18 with a filter 19 to allow the air out. The adjustable relief valve can also make the internal pressure adjustable depending on how the device is being used, particularly if the unit is used as a non-invasive ventilator. The relief valve is attached to the port 18 on the enclosure. The port 18 may have a low-profile mount frame to attach the air hose 20 or the relief valve itself, allowing one to switch the relief valve or to make filters that can be swapped out.

The enclosure 2 may be in shape of a helmet 23 as shown in FIG. 2. The helmet 23 includes a side wall 21 provided with the filter 22 for filtering air and allow sound to travel into and out of the helmet. The ports 15, 18 and 26 may also be provided as needed. The helmet 23 includes a transparent window 25 to allow the use to see out. The helmet 23 is made of rigid plastic material that advantageously holds its form.

Referring to FIG. 3, the enclosure 2 is provided with tie-down straps 27 that may be clipped to the user's protective gown or clothing during use to minimize the enclosure 2 from moving from side to side. The straps 27 may be attached along the corners of the enclosure 2.

Figure 4:
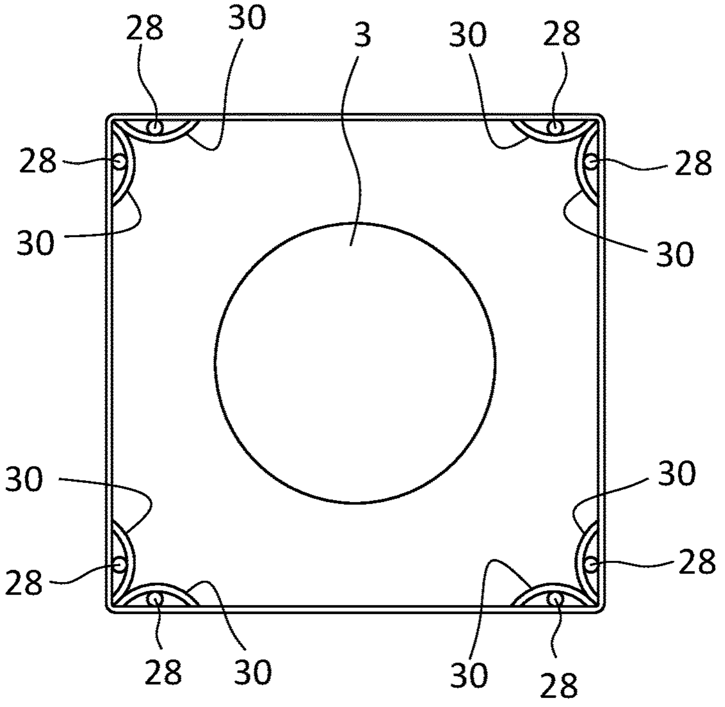
FIG. 4 is cross-sectional view taken along line 4-4 in FIG. 3.

Referring to FIGS. 3 and 4, the enclosure 2 uses a frame made of spring wire loops 28 attached to the respective vertical walls 32 to hold the shape of the enclosure 2 in the expanded configuration. Each wall 32 has a sleeve 30 along the edge portions of the wall. The wire loops 28 are disposed in the respective sleeves 30. Each of the spring wire loops 28 is made from a length of spring wire, preferably steel, with ends joined end-to-end with a coupling, by welding or other standard connectors to form a continuous loop. Potential energy is stored in the spring wire when turned into a loop. The tendency of the loop to expand outwardly to return to its original straight line due to its stored energy when bent into a loop makes the walls 32 self-supporting in the flat configuration. The spring wire loops 28 will pull and stretch the material of the wall 32 outwardly. The spring wire has relatively small cross-section compared to its length to allow the twisting and folding of the walls 32. The spring wire may be of other cross-sectional shapes, such as round, square, etc.

While the springs 28 are shown attached to the four vertical side walls 32, it should be understood that the springs 28 may be equally arranged in a different configuration, such as attaching to the top wall, and two opposite vertical side walls to provide the frame for the enclosure when expanded.

Figure 5D:
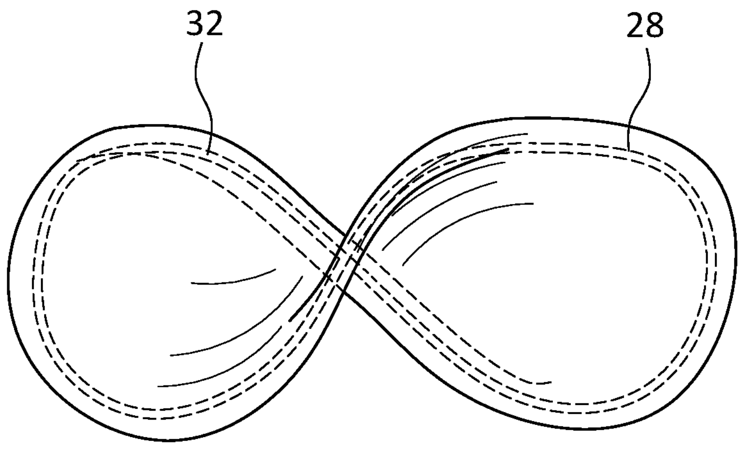
Figure 5E:
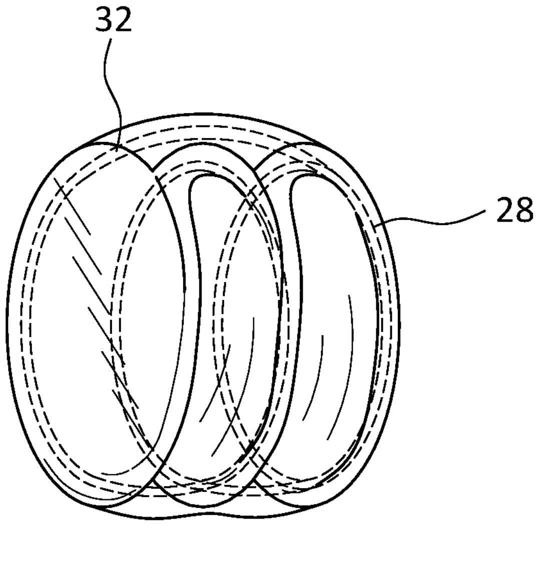

The enclosure being made of foldable and flexible material may be folded flat into a compact shape for storage or shipping. The enclosure 2 is preferably shaped like a rectangular prism with a square cross-section as shown in FIG. 4 for ease of folding. Referring to FIGS. 5A-5E, the enclosure 2 is folded flat by bringing the adjacent walls 32 on top of each other, as shown in FIG. 5A. The flattened enclosure is then folded unto itself along the separation between the adjacent walls 32, as shown in FIG. 5B to arrive at a configuration where the walls 32 are stacked one on top of the other, as shown in FIG. 5C. The configuration of FIG. 5C is then twisted into a figure "8," as shown in FIG. 5D and folded onto itself, as shown in FIG. 5E, resulting in a flattened and compact configuration for the enclosure 2 for storage or shipping. The straps 27, pouch or plastic wrapping may be used to hold the enclosure 2 in the folded configuration since the process of flattening the enclosure 2 creates potential energy in the wire loops 32, urging the wire loops 32 to spring back to their single loop configuration. To deploy the folded enclosure 2 prior to use, the restraint is removed and the wire loops 32 are allowed to spring back to their original single loop configuration.

Figure 6A:
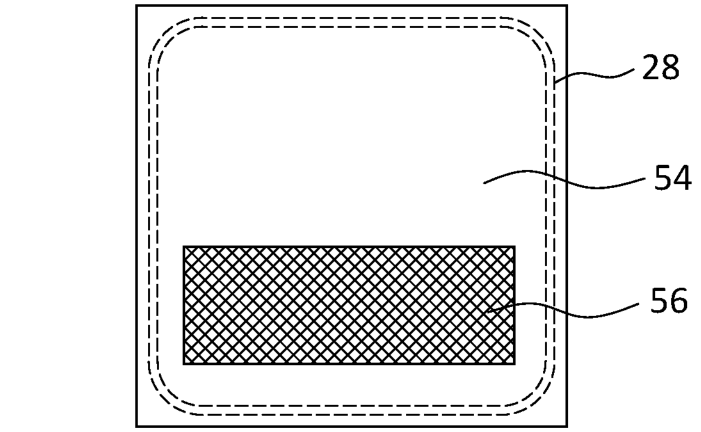
FIGS. 6A-6C show the placement of filter patches around the enclosure.

Referring to FIG. 6A, the front wall 54 of the enclosure 2 is provided with a filter patch 56, which is advantageously disposed at a lower portion of the front wall 54 below the user's eyes and preferably in front of the user's mouth and nose to minimize any fogging of the front wall from the user's breath. The filter patch 56 is operably attached to the wall 54 by sewing, adhesives, VELCRO fasteners and tape to seal the edges, or other standard means. Although shown as rectangular, the filter patch 56 may be of any shape, such as square, round, oblong, triangular, etc. The filter patch 56 may occupy the bottom ⅓ or larger of the front wall 56 as needed. The front wall 54, except where the filter patch 56 is located, is clear to enable the user to see outside. The filter patch 56 can be as large as needed without obscuring the user's vision.

Figure 6B:
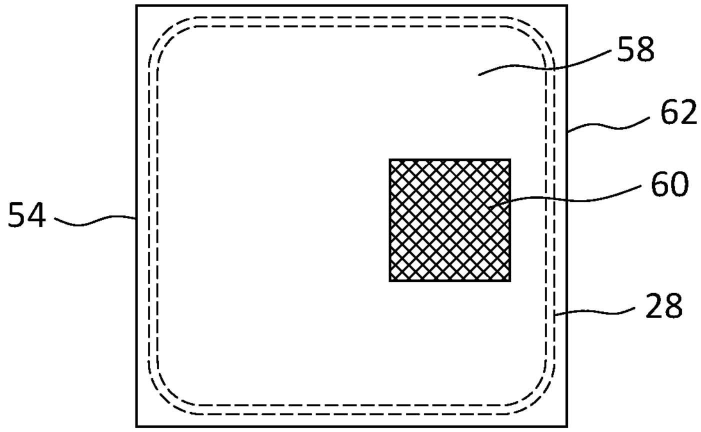

Referring to FIG. 6B, the left side wall 58 is provided with a filter patch 60 advantageously at the rear portion near the user's ear so as not to obscure the user's peripheral view or when he turns sideways. The filter patch 60 advantageously helps in the sound travel during a conversation while using the enclosure 2. The left side wall 58, except where the filter patch 56 is located, is clear to enable the user to see outside through his peripheral field of view. The filter patch 60 is operably attached to the left wall 58 by sewing, adhesives, VELCRO fasteners and tape to seal the edges, or other standard means. The shape of the filter patch 60 may be of any shape, such as square, round, oblong, triangular, etc. The right side wall is a mirror image of the left side wall 58 and is structurally similar with its own filter patch.

Although both the left side and right walls are disclosed as having the filter patches 60, it should be understood that the enclosure 2 may only need the left side wall or the right side wall to have the filter patch 60.

Figure 6C:
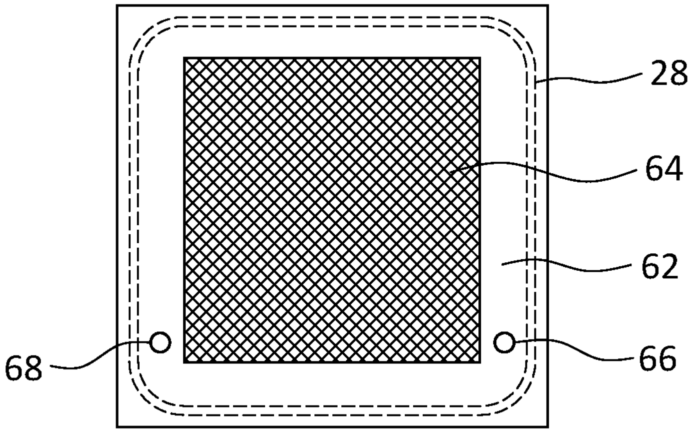

Referring to FIG. 6C, the rear wall 62 may be provided with a filter patch 64, which is preferably as large as needed. The filter patch 64 may be of any shape, such as square, round, oblong, triangular, etc. The filter patch 64 may be operably attached to the wall 62 by sewing, adhesives, VELCRO fasteners and tape to seal the edges, or other standard means. The top wall may also be provided with its own filter patch in a similar way as the rear wall 62. The back wall and the top wall, if provided with filter patches, will advantageously increase the amount of air exchanges between the interior and exterior of the enclosure 2. The back and top walls may be opaque or clear outside of the filter patch 64.

The back wall 62 may also be provided with an air inlet port 66 for connection of the tube 10, filter 12 and blower 14. The blower will provide additional air to the user in conjunction with the filter patches but in case of blower malfunction, the filter patches will continue to provide air to the user.

The enclosure 2 also includes a top wall on which a filter patch may be attached in the same manner as the filters 56, 60 and 64. The filter patch may be as large as large as needed, such as the filter patch 64 on the back wall 62.

Although the filters 56, 60 and 64 are shown in patch or sheet form, the filters may also be of a cartridge type that can be easily screwed on, snapped in place or otherwise attached by standard means to the enclosure. The cartridge type filter advantageously allows for quick filter replacement as needed without the need to replace the enclosure 2 when used by the same user.

An embodiment of the device 1 may include the enclosure 2 with only the air inlet port 66 connected to the blower 14 for air supply and a relief valve 68 for regulating the pressure inside the enclosure 2. The relief valve 68 may be adjustable to the pressure inside the enclosure 2 and may also include a filter. Although shown in the back wall 62, the relief valve 68 may be attached anywhere on the enclosure walls.

The device 1 as described above will help to contain pathogens within the enclosure when used on sick people with contagious pathogens, or to keep pathogens out of the device if used by a caregiver, and could also serve as a non-invasive ventilator for sick people with respiratory illness.

The device, although applicable to similar circumstances via ventilation, can have the benefit of merely serving as a containment system for patients with less severe conditions as well as a scenario for self-isolation where one would want to contain one's sickness and pathogens from spreading to other household members, patients or caregivers.

A caregiver could also wear it to protect himself in a scenario where a pandemic, epidemic or other airborne pathogen or contaminant is present. It can also be used as a pressurized ventilator for people with respiratory illness.

The device can have the added benefit of allowing for better communication between patient and doctor by way of the filter patches that allow for better sound travel, than existing units made completely out of plastic. Placement of the filter patches 60 near the user's ears advantageously facilitates conversations between the user and another person.

The device also allows for the enclosure 2 to maintain its shape with very little weight and it can be collapsible to a flat form, and easily shipped for emergency scenarios such as pandemics. If power goes out, the enclosure 2 can maintain its shape and the passive filter patches can allow for the user to continue breathing, and air to continue to be filtered both in and out.

The enclosure 2 can be a variety of shapes. Preferably the enclosure 2 is shaped like a cube or a rectangular prism to afford the user a relatively flat clear flat surfaces (for example, as compared to a cylindrical surface) to look through with reduced or minimum image distortion.

Figure 7:
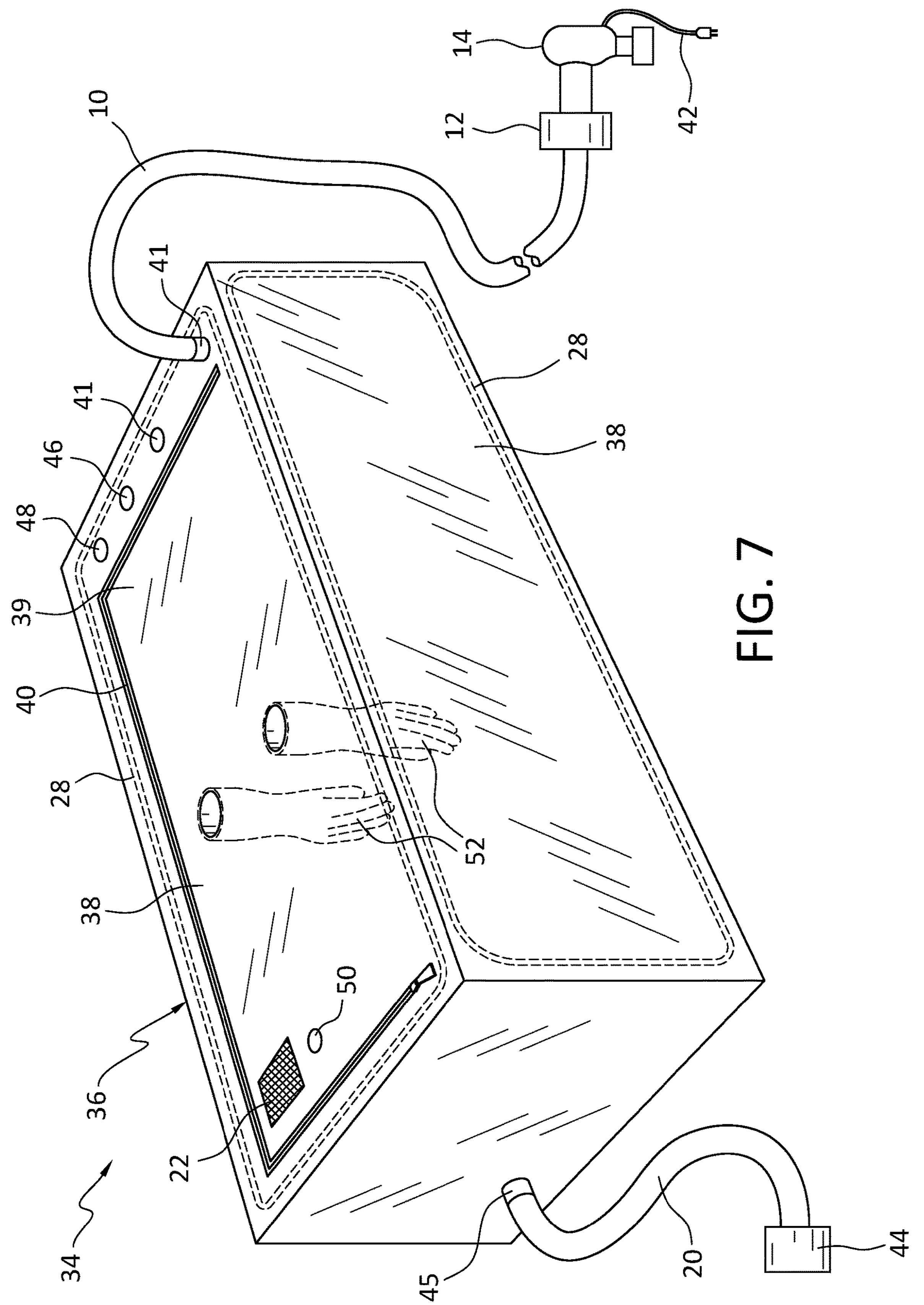
FIG. 7 is a full-body version of the device of FIG. 1.

Referring to FIG. 7, the device 1 is modified as a full body sized pathogen containment and ventilator device 34 with an enclosure 36 made of air-tight material configured to enclose an entire person's body.

The enclosure 36 is preferably shaped like a rectangular prism with the walls 38 have the same width to form a square cross-section for ease of folding. The enclosure 36 is preferably made of transparent or clear plastic to minimize the feeling for the user of being enclosed. The walls 38 afford the user a relatively flat clear surface (as compared to a cylindrical surface) to look through with reduced or minimum image distortion.

The enclosure 36 may be made of foldable and flexible material clear plastic sheet, a combination of clear plastic sheet and opaque plastic sheet or air-tight fabric material, to help contain air within the enclosure. As with the enclosure 2, the enclosure 36 is supported in the expanded position by the spring wire loops 28 disposed inside the sleeves 30 along the edge portions of the walls 38.

An air-tight zipper 40 running along the edge portions of the top wall 39 defines an opening for placing the patient inside the enclosure 36. The top wall 39 serves as a sealable cover for the opening when joined to the enclosure by the zipper 40. A flap may be installed along one side of the zipper 40 and removably attached along the other side with VELCRO to further seal the zipper.

Air is supplied to patient inside the enclosure 36 through the tube 10, filter 12 and blower 14. The tube 10 is detachably attached to the enclosure 36 through a port 41. The blower 14 may be directly connected to a wall outlet through a cord and plug 42. The battery pack 16 may be also used while the patient is being transported to a different location. The filter 12 filters incoming air prior to entering the enclosure to keep the patient inside from external pathogens. The blower 14 may be either in front of or behind the filter 12.

Air is exhausted through the tube 20 and filter 44. The tube 20 is attached to a port 45 with a detachable mount. The port may include an adjustable relief valve. The port 45 is closed and sealed when not in use.

The filter patch 22 may be also used for exhausting air from inside the enclosure 36. Several filter patches 22 on several walls of the enclosure 36 may be used for increased air flow. The filter patches passively filter the air flowing out of the enclosure 36. The filter patches can either be sewn, glued, attached with VELCRO fasteners and tape to seal the edges, or otherwise attached by standard means directly to the walls. The filter patches advantageously allow sound to travel from the outside to the inside of the enclosure and vice versa to enable voice communication between the patient and a caregiver, since the filter material is a better sound conductor than a sheet of plastic.

The exhaust tube 20 and the filter 44 may be used to replace the filter patches 22 when the device 34 is used as a ventilator to advantageously regulate the inside pressure. The tube 20 is detachably attached to the enclosure 36 through a port 49.

A port 50 with a removable filter may be used instead of filter patches 22. The port 50 may include an adjustable relief valve with a filter to allow air out and make the internal pressure inside the enclosure adjustable depending on the use of the device 34, particularly if the device 34 is used as a non-invasive ventilator. The port 50 preferably has a low-profile mount frame for attaching to an air hose, or the relief valve itself, allowing one to switch the relief valve or to use filters that can be swapped out. The port 50 is closed and sealed when not in use.

A port 46 may be used to supply the patient with direct inlet from a respirator, if needed, such as an in-mouth or over-mouth respirator. Another port 48 may be provided for supplemental oxygen, or other medical gas mixtures that may be needed. Mounts on all ports may have frames for attaching or detaching various filters tubes, relief valves etc. The ports are sealed closed when not in use.

Sealed gloves 52 may be provided to allow doctors or other caregivers to move or touch the patient while avoiding contact with pathogens.

The enclosure 36 is folded into a flat and compact configuration in the same way as the enclosure 2, as shown in FIGS. 5A-5E. With its compact configuration, the enclosure 36 advantageously occupies a relatively small space for storage or shipping.

The device 34 advantageously helps to contain pathogens within the enclosure when used on sick people with contagious pathogens, or to keep pathogens out of the device if used by a caregiver, and could also serve as a non-invasive ventilator for sick people with respiratory illness.

The device 34 provides the benefit of merely serving as a containment system for patients, or also serving the same functions as existing containment bubbles where one would want to contain their sickness and pathogens from spreading to other patients or caregivers.

The device 34 can also be used as a pressurized ventilator for people with respiratory illness. The device can have the added benefit of allowing for better communication between patient and doctor by way of the filter patches allowing for better sound travel, than existing units made completely out of plastic.

The device 34 also allows for it to maintain its shape with very little weight and it can be collapsible to a flat form, and easily shipped for emergency situations, such as pandemics. If power goes out the device can maintain its shape and its passive filters can continue allow for the user inside the enclosure 36 to continue breathing, and air to continue to be filtered both in and out.

Figure 8A:
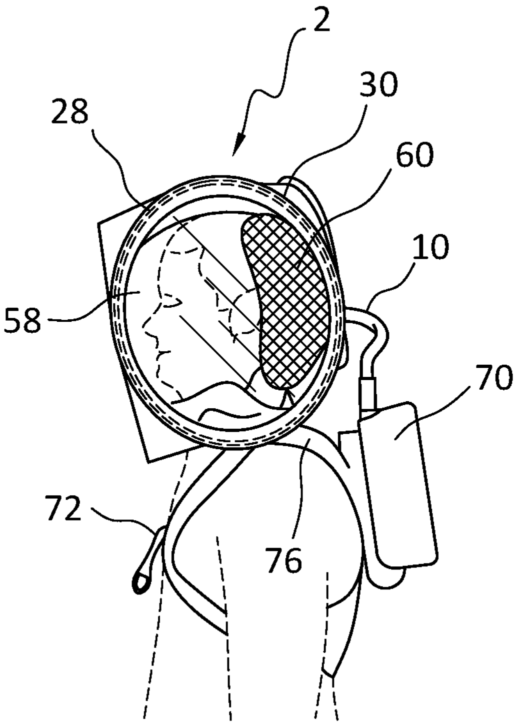
FIGS. 8A-8C show an embodiment of the pathogen protection device shown in FIG. 1.
Figure 8B:
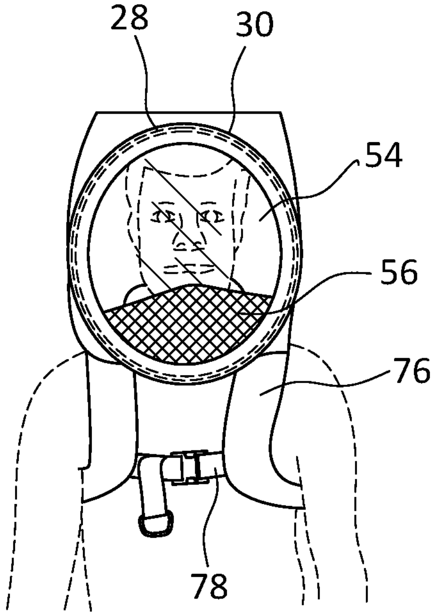
Figure 8C:
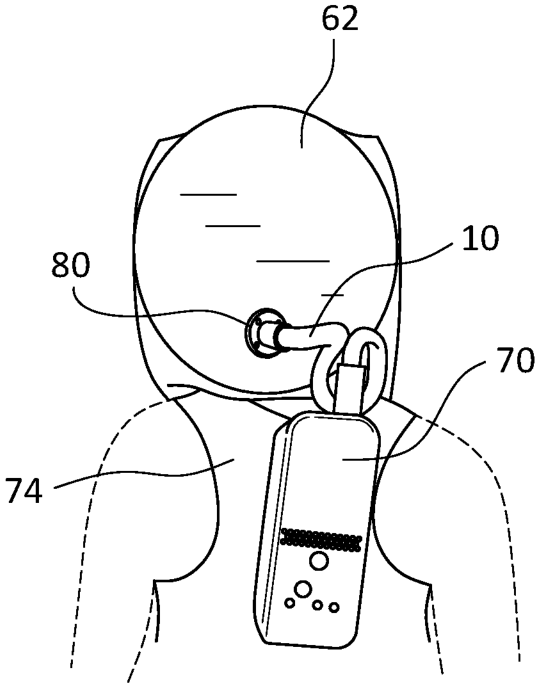

Referring to FIGS. 8A-8C, the breathing device 1 is shown worn by a user. Although the enclosure 2 is somewhat rounded than shown in FIG. 3, the construction and operation of the breathing device is the same as that shown in FIG. 3.

Referring to FIG. 8A, the filter patch 60 is shown with a different size and shape than shown schematically in FIG. 6B, but works the same way for allowing sound travel during conversation with the user. Referring to FIG. 8B, the filter 56 is shown with a different shape without detracting from its purpose of minimizing fogging of the front wall and allowing sound to travel through during conversation. Referring to FIG. 8C, the rear wall 62 is shown made of an air-tight fabric material.

Referring to FIGS. 8A and 8C, a power unit 70 includes the filter 12, the blower 14 and the battery pack 16. The power unit 70 is operably attached to a carrier 72 worn by the user. The carrier 72 includes a backwall 74 attached to shoulder straps 76 and chest strap 78.

The tube 10 communicates with the interior of the enclosure 2 at one end and with the blower 14 at the other end. A quick disconnect coupling 80 advantageously allows for quickly disconnecting the tube 10 from the enclosure 2 by hand without tools after use by one user to allow a fresh enclosure 2 to be connected to the power unit 70 for use by another user.

Figure 9A:
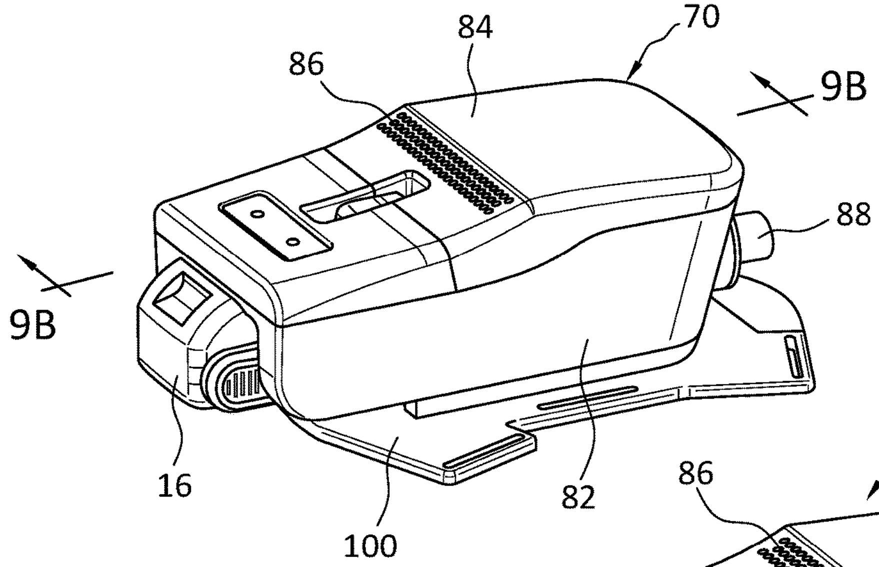
FIG. 9A shows an embodiment of a power unit comprising the blower, filter and battery shown in FIGS. 1 and 8A.
Figure 9B:
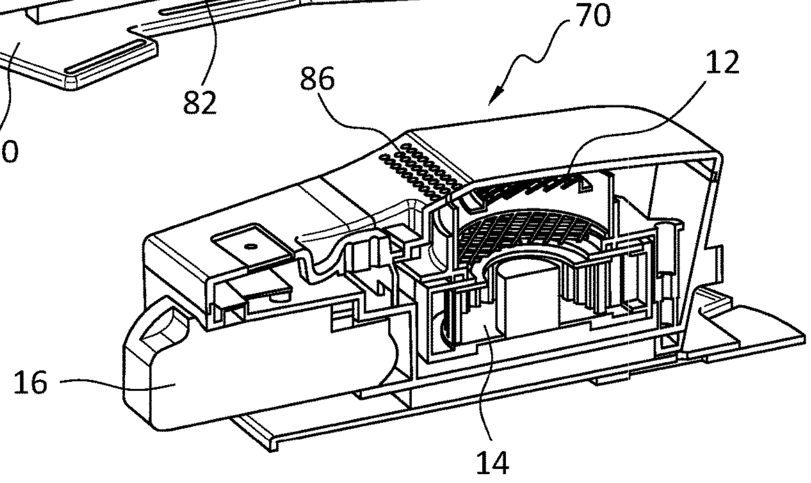
FIG. 9B is a cross-sectional view of FIG. 9A taken along line 9-9.

Referring to FIGS. 9A and 9B, the power unit 70 includes a housing 82 with a removable cover 84 for access to the filter 12. The battery pack 16 is insertable into the housing through an opening 83 in the housing 82. The housing 82 includes an air inlet 86 and air outlet 88. The power unit 70 is detachably attached to a backwall 100, which is operably attached to the shoulder straps 76.

Figure 9C:
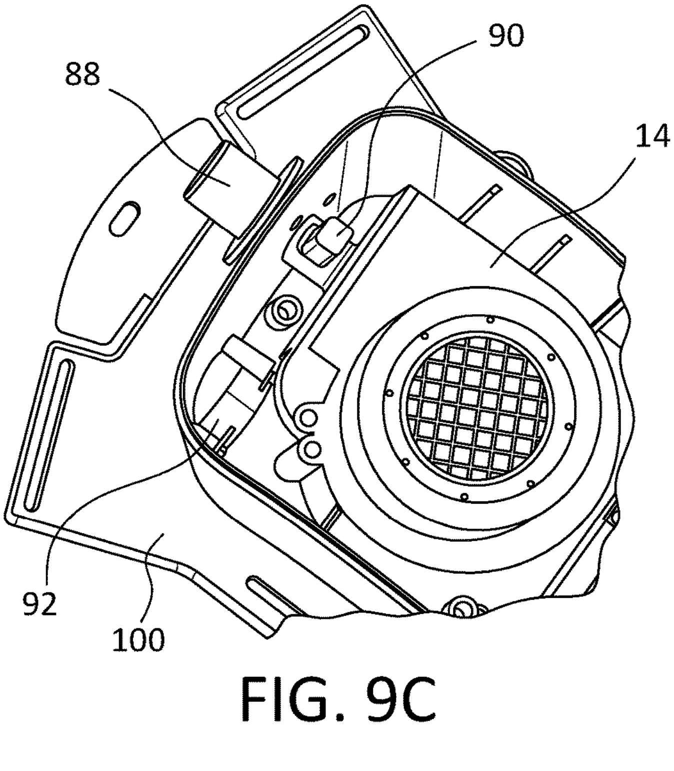
FIG. 9C is a partial view of FIG. 9A with the top cover removed.

Referring to FIG. 9C, a flow sensor 90 is provided downstream of the air outlet 88 to advantageously sense the air flow into the enclosure 2 when the breathing device 1 is in use. An audible alarm 92 is triggered when the airflow stops, for example when the battery runs out, advantageously signaling the user to move to a safe place where he can remove the enclosure 2.

Figure 10:
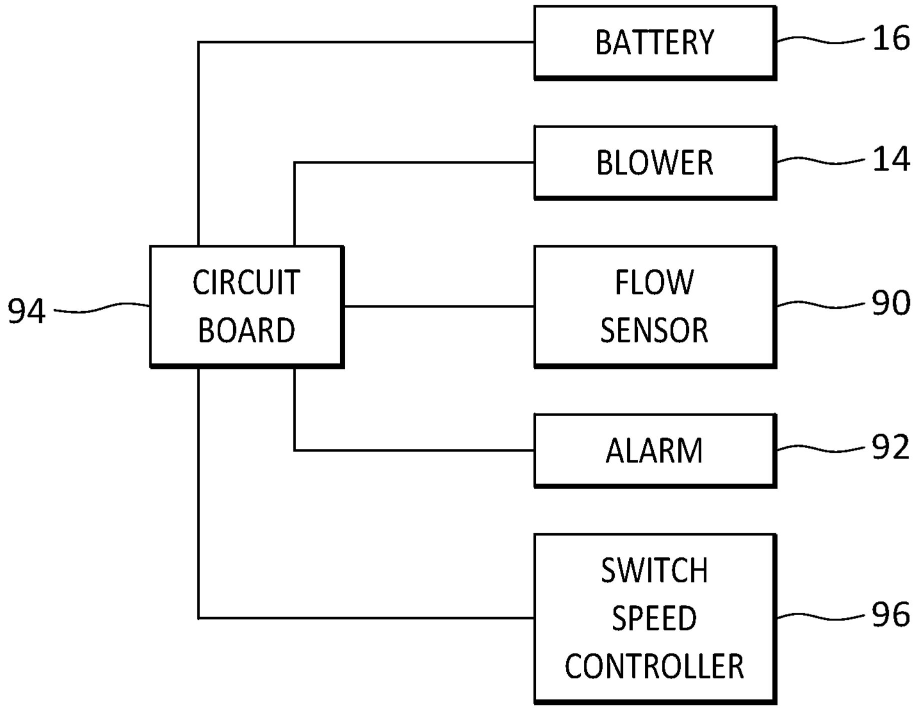
FIG. 10 is a functional block diagram of the electrical components used in the present invention.

Referring to FIG. 10, a circuit carried on a circuit board 94 provides for controlling the blower 14 through an on/off switch 96 and for increasing or decreasing the speed of the blower 14. The flow sensor 90 activates the alarm 92 when airflow through the air outlet 88 stops. The circuit board 94 regulates the battery voltage and controls the blower speed by standard means, such by varying the supply voltage. The circuit board 94 is designed to send power to the blower 16 from the battery 14 and to activate the alarm 90 when airflow ceases while the unit is still powered. The circuit is of standard design within the skill of a person of ordinary skill in the art. The circuit board 94 is preferably disposed inside the housing 82.

Figure 11A:
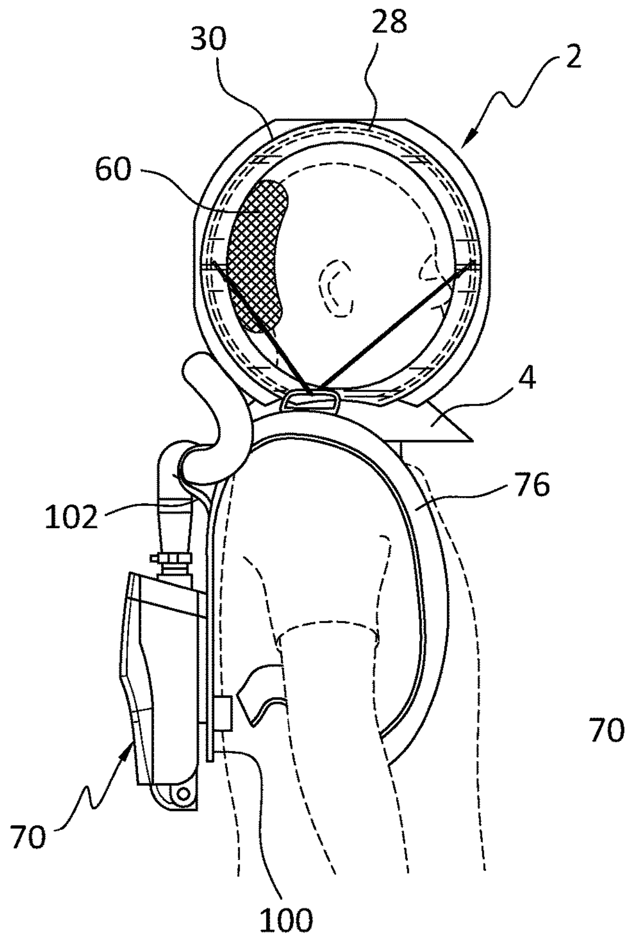
FIGS. 11A-11D show another embodiment of the pathogen protection device shown in FIG. 1.
Figure 11B:
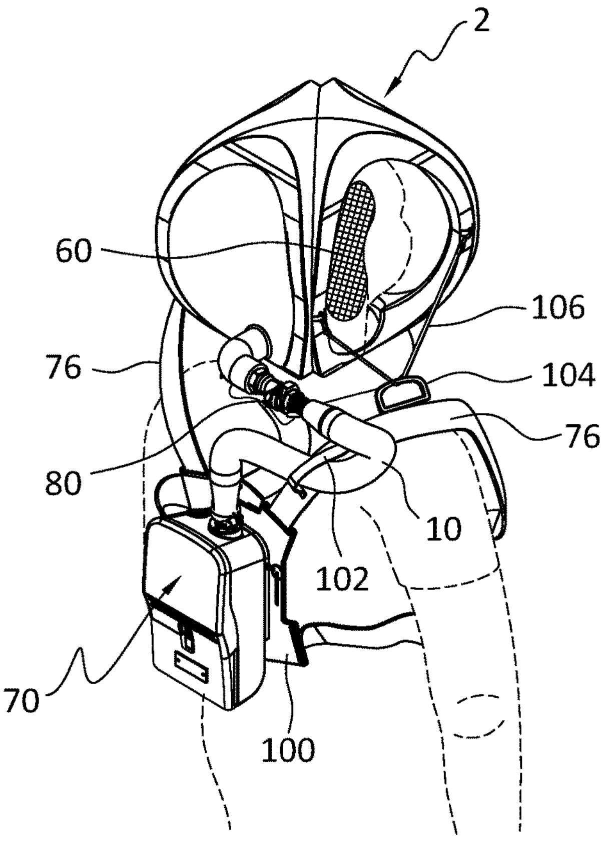
Figure 11C:
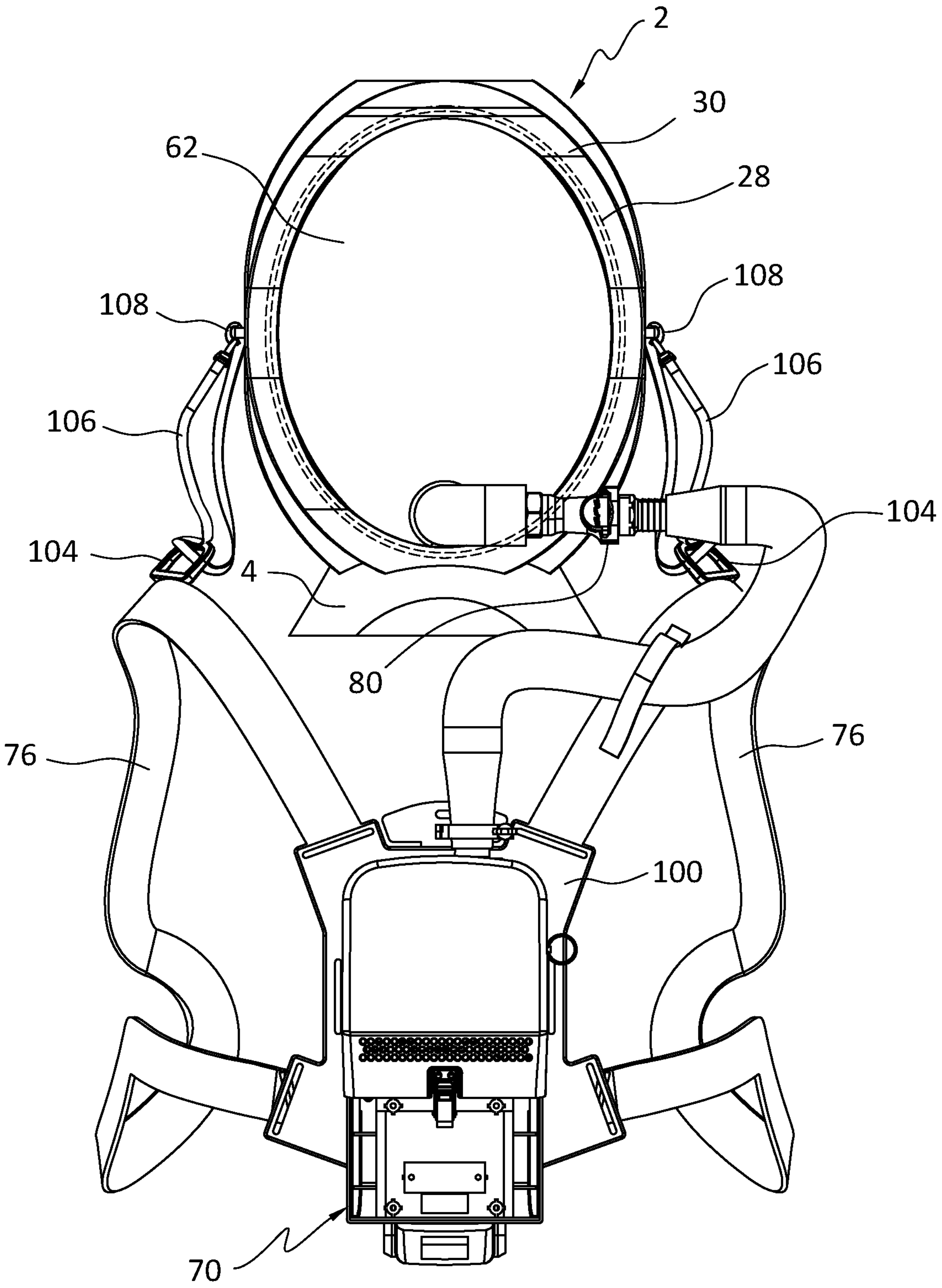
Figure 11D:
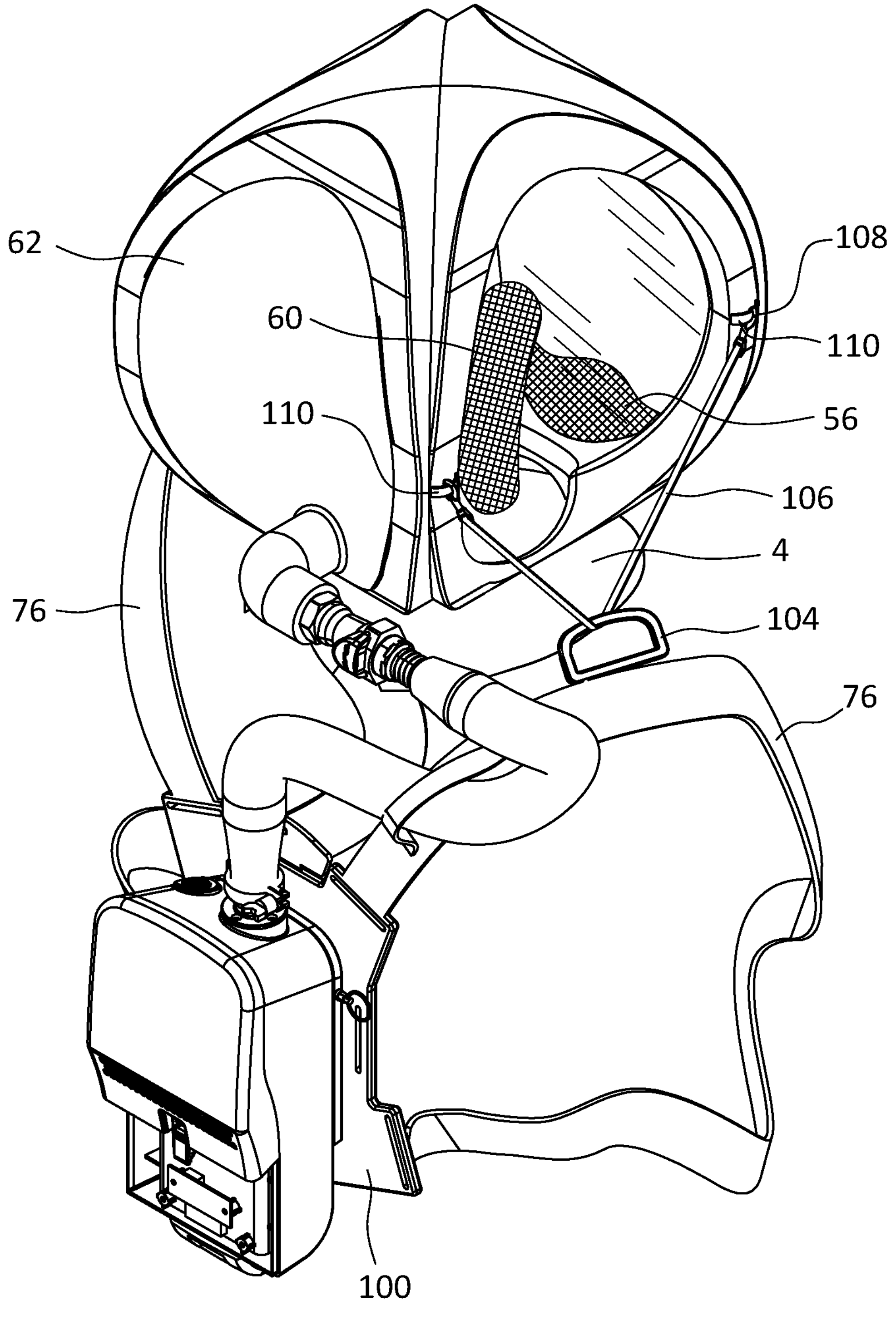

Referring to FIGS. 11A, 11B and 11C, the power unit 70 is advantageously detachably mounted on the backwall 100 carried on the user's back below the shoulders and preferably closer to the waistline. A chest strap 78 or waist strap may be added to advantageously stabilize the shoulder straps 76 and transfer some of the weight of the power unit 70 to other parts of the user's body. The tube 10 may be stabilized with a strap 102 tied to the shoulder strap 76.

A ring 104, such as "D" ring 104, is attached to each of the shoulder straps 76. A tie-down strap 106 is looped through each of the rings 104 and operably attached to the left side and the right side of the enclosure 2. The tie-down straps 106 are advantageously adjustable in length to remove any slack so as to hold the straps 106 taut between the enclosure 2 and the shoulder straps 76. The ends of the straps 106 are provided with clips 108 detachably attached to loops 110 on the enclosure 2 for easy detachment of the straps 106 from the enclosure 2 to permit removal of the enclosure 2 after use.

The enclosure 2 is shown in FIGS. 11A-11D with a different shape due to the top wall and the bottom wall being smaller than the side walls.

Although the enclosure 2 is shown with the blower 12, the enclosure 2 may be used without the blower 12, relying on the filter patches 56, 60 for supplying air to the user.

While this invention has been described as having preferred design, it is understood that it is capable of further modifications, uses and/or adaptations following in general the principle of the invention and including such departures from the present disclosure as come within known or customary practice in the art to which the invention pertains, and as may be applied to the essential features set forth, and fall within the scope of the invention or the limits of the appended claims.

We claim:

1. A pathogen protection device, comprising:

a) a foldable enclosure made of air-tight material configured to enclose a top and a plurality of sides of a user's head, the enclosure being a wearable hood configured to allow the user to see through, the enclosure including a bottom opening for placing the enclosure around the user's head, the opening including a neck seal configured to seal the user's head from outside the enclosure, the neck seal is configured to be disposed around a neck of the user;

b) the enclosure including a first side wall and a second side wall adjacent to the first side wall;

c) the first side wall including a first edge portion and a first sleeve disposed along the first edge portion, the second side wall including a second edge portion and a second sleeve disposed along the second edge portion;

d) a first spring wire loop is disposed in the first sleeve, a second spring wire loop is disposed in the second sleeve, the first spring wire loop and the second spring wire loop being configured to outwardly stretch the first side wall and the second side wall, respectively, the first side wall comprising a first panel stretched by the first spring loop, the second side wall comprising a second panel stretched by the second spring wire loop; and e) a filter operably associated with the enclosure to allow air to be filtered before entering and exiting the enclosure, the filter being configured to remove pathogens from the air entering and exiting the enclosure, the filter to allow sound travel through the enclosure for voice communication between the user and a person outside the enclosure;

whereby, when the foldable enclosure is worn by the user, an interior surface of the first panel is configured to face a first side of the plurality of sides of the user's head and an interior surface of the second panel is configured to face a second side of the plurality of sides of the user's head.

2. The pathogen protection device as in claim 1, wherein the filter is disposed on the first side wall of the enclosure.

3. The pathogen protection device as in claim 1, wherein the filter is disposed on the second side wall of the enclosure.

4. The pathogen protection device as in claim 1, wherein the enclosure includes an auxiliary port for attaching to a supply of oxygen.

5. The pathogen protection device as in claim 1, and further comprising a blower for supplying pathogen filtered air to the enclosure.

6. The pathogen protection device as in claim 5, wherein the blower is configured to be attachable to the user's body.

7. The pathogen protection device as in claim 6, and further comprising:

a) a carrier including a backwall and shoulder straps operably attached to the backwall; and b) the blower is operably attached to the backwall.

8. The pathogen protection device as in claim 5, wherein:

a) the blower includes a housing; and b) the housing includes an opening for inserting a battery.

9. The pathogen protection device as in claim 1, and further comprising tie-down straps operably attached to the enclosure to stabilize the enclosure.

10. The pathogen protection device as in claim 1, wherein the enclosure includes straps for attaching to the user's clothing.

11. The pathogen protection device as in claim 1, wherein the first side wall forms a transparent front wall.

12. A pathogen protection device, comprising:

(a) an enclosure made of air-tight material, the enclosure being a wearable hood configured to allow a user to see through, the enclosure having a left side wall and a right side wall;

(b) a filter is disposed on the left side wall and/or the right side wall of the enclosure, the filter to allow filtered air to enter and exit the enclosure, the filter is configured to remove pathogens from the air entering and exiting the enclosure;

(c) a front side wall and a back side wall;

(d) a stretchable neck ring formed at a bottom end portion of the enclosure, the stretchable neck ring being configured to seal the enclosure around a neck of the user; and (e) the front side wall, the left side wall, the right side wall, and the back side wall each including a spring loop to operably stretch each of the front side wall, the left side wall, the right side wall, and the back side wall outwardly, each of the front side wall, the left side wall, the right side wall and the back side wall includes an edge portion and a sleeve disposed along the edge portion; and the spring loop of each of the front wall, the left side wall, the right side wall and the back wall is disposed inside the respective sleeve of each of the front wall, the left side wall, the right side wall and the back wall, the enclosure is configured to surround the user's head such that the front side wall corresponds to a face of the user, the back side wall corresponds to a back of the user's head, the left side wall corresponds to a left side of the user's head and the right side wall corresponds to a right side of the user's head, and wherein the enclosure is foldable and when the pathogen protection device is being worn by the user, the user's face is visible through the front wall and through an area formed by the spring loop of the front wall.

13. A pathogen protection device, comprising:

a) a foldable enclosure made of air-tight material configured to enclose a top and a plurality of sides of a user's head, the enclosure being a wearable hood configured to allow the user to see through, the enclosure including a bottom opening for placing the enclosure around the user's head, the opening including a neck seal configured to seal the user's head from outside the enclosure, the neck seal is configured to be disposed around a neck of the user;

b) the enclosure including a first wall and a second side wall adjacent to the first side wall, the first side wall including a first edge portion and a first sleeve disposed along the first edge portion, the second side wall including a second edge portion and a second sleeve disposed along the second edge portion;

c) a first spring wire loop is disposed in the first sleeve, a second spring wire loop is disposed in the second sleeve, the first spring wire loop and the second spring wire loop being configured to outwardly stretch the first side wall and the second side wall, respectively, the first side wall comprising a first panel stretched by the first spring loop, the second side wall comprising a second panel stretched by the second spring wire loop;

d) an exhaust port operably associated with the enclosure; and e) a blower and a first filter configured to remove pathogens from the air, the blower for supplying pathogen filtered air into the enclosure;

whereby, when the foldable enclosure is worn by the user, an interior surface of the first panel is configured to face a first side of the plurality of sides of the user's head and an interior surface of the second panel is configured to face a second side of the plurality of sides of the user's head.

14. The pathogen protection device as in claim 13, wherein the blower is attachable to the user's body.

15. The pathogen protection device as in claim 13, and further comprising:

a) a carrier including a backwall and shoulder straps operably attached to the backwall; and b) the blower is operably attached to the backwall.

16. The pathogen protection device as in claim 13, wherein:

a) the blower includes a housing; and b) the housing includes an opening for inserting a battery.

17. The pathogen protection device as in claim 13, wherein the exhaust port includes a second filter.

* * * * *